United States Patent [19]

Yang et al.

[11] Patent Number: 4,515,722

[45] Date of Patent: May 7, 1985

[54] PHOSPHATIDYL INOSITOL ANALOGS USEFUL AS ANTI-INFLAMMATORY/ANALGESIC AGENTS

[75] Inventors: Shu S. Yang, Bridgewater; Thomas R. Beattie, Scotch Plains; Philippe L. Durette, New Providence; Timothy F. Gallagher, Metuchen; Tsung-Ying Shen, Westfield, all of N.J.

[73] Assignee: Merck & Co., Inc., Rahway, N.J.

[21] Appl. No.: 362,632

[22] Filed: Mar. 30, 1982

[51] Int. Cl.$^3$ ............................ C07F 9/10; C07F 9/08; C07F 9/113; A61K 31/66

[52] U.S. Cl. .................... 260/403; 260/349; 260/455 P; 260/928; 260/940; 260/941; 260/944; 260/948; 260/949; 260/953; 260/954

[58] Field of Search ............... 260/403, 349, 970, 941, 260/944, 948, 949, 928, 953, 954, 455 P

[56] References Cited

U.S. PATENT DOCUMENTS 3,632,627  1/1972  Gordon et al. ................. 260/403 X
3,704,254  11/1972  Aneja ............................. 260/403
4,129,650  12/1978  Betzing et al. ................. 260/403 X

FOREIGN PATENT DOCUMENTS 2659048  12/1976  Fed. Rep. of Germany .
740740  10/1977  U.S.S.R. .
740749  3/1978  U.S.S.R. .

OTHER PUBLICATIONS

Engel, Chem. Review, 77, (3), p. 349 (1977).
V. A. Sukhanou et al., Zh. Obs. Khim. (Eng. translation), 47, 2130 (1977).
R. Sundler et al., J. Biol. Chem., 253, 4175 (1978).
P. D. Wightman, Biochem. J. 197, 523 (1981).

*Primary Examiner*—Thomas A. Waltz
*Attorney, Agent, or Firm*—Theresa Y. Cheng

[57] ABSTRACT

Phosphatidyl inositol analogs are found to be effective phospholipase C inhibitors and thereby potent anti-inflammatory and analgesic agents. These phosphatidyl inositol analogs are prepared by condensation of a protected inositol with a substituted phosphonic or phosphorous acid followed by removal of protecting groups.

3 Claims, No Drawings

PHOSPHATIDYL INOSITOL ANALOGS USEFUL AS ANTI-INFLAMMATORY/ANALGESIC AGENTS

BACKGROUND OF THE INVENTION

A group of novel phosphatidyl inositol (PI) analogs are found to be effective phospholipase C inhibitors which are useful anti-inflammatory and analgesic agents.

Phospholipase C contained in mouse peritoneal macrophages has been linked to the enhanced turnover of phosphatidyl inositols which in turn has been suggested by recent studies as one of the sources of arachidonic acid. It has been established that a rapid synthesis of prostaglandins (PG) from arachidonic acid in macrophages usually accompanies inflammatory stimuli. Thus, inhibition of the release of arachidonic acid from macrophages would provide an effective control of PG synthesis and thereby inflammatory conditions. Recently, phospholipase C has been characterized as an enzyme which is involved in the biosynthetic phosphatidylinositol-arachidonic acid-prostaglandin pathway. This finding is further substantiated by the observation that phospholipase C is inhibited by phenothiazine, a compound known to inhibit the stimulated release of arachidonic acid from macrophages and prostaglandins from platelets.

Accordingly, it is an object of this invention is provide specific and selective inhibitors of phospholipase C which can be potent anti-inflammatory and analgesic agents useful in the treatment of inflammatory conditions, including rheumatoid arthritis, emphysema, bronchial inflammation, osteoarthritis, spondylitis, lupus, psoriasis, acute respiratory distress syndrome, gout, fever, and pain.

Another object of this invention is to provide pharmaceutical compositions to be used in the administration of the novel phospholipase C inhibitors, which are novel phosphatidyl inositol analogs.

Still a further object of this invention is to provide a method of controlling and treating inflammation and pain by administering an effective amount of the novel phosphatidyl inositol analogs in a mammalian species in need of such treatment.

Finally, it is also an object of this invention to provide a process for preparing the novel phosphatidyl inositol analogs.

DETAILED DESCRIPTION OF THE INVENTION

This invention relates to novel phosphatidyl inositol analogs of the structural formula I.

$$L-\underset{\underset{OR}{|}}{\overset{\overset{O}{\|}}{P}}-Y-A \quad (I)$$

or a pharmaceutically acceptable acid, ester, ether or carbonate thereof, wherein:

L is
(a) hydrogen;
(b) $R^1$; where $R^1$ is
  (1) straight or branched-chain alkyl having from 1 to 20 carbon atoms especially $C_{7-20}$ alkyl, such as n-heptyl, n-decyl, isododecyl, n-pentadecyl, n-hexadecyl, n-octadecyl, and n-eicosyl;
  (2) aryl having from 6 to 10 carbon atoms especially phenyl, substituted phenyl or naphthyl;
  (3) cycloalkyl having from 3 to 8 carbon atoms, especially cyclopentyl or cyclohexyl.
  (4) alkenyl having from 2 to 20 carbon atoms especially $C_{8-20}$ alkenyl such as n-octenyl, i-decenyl, i-dodecenyl, n-tetradecenyl, n-octadecenyl, nonadecenyl or arachidonyl;
  (5) cycloalkenyl having from 5 to 8 carbon atoms, especially cyclopentenyl or cyclohexenyl;
  (6) aralkyl, alkaryl, aralkenyl, alkenylaryl, wherein alkyl, aryl, and alkenyl are as previously defined;

The above groups (1) to (6) are unsubstituted or substituted by radicals, for example, hydroxy; alkoxy; halo such as fluoro, chloro, bromo or iodo; cyano; carboxy; amino; substituted amino such as mono $C_{1-6}$ alkylamino and di($C_{1-6}$ alkyl) amino; carbamoyl; sulfonyl; sulfinyl; thio; alkylthio, nitro or the like. Representative examples of these substituted groups are hydroxyethyl, 3-methoxypropyl, 4-hydroxyphenyl, 3- or 4-chlorobenzyl, 4-trifluorobenzyl, 2-aminophenethyl, 2-carboxyphenylethenyl, 4-cyanomethylphenyl, 4-(N,N-dimethylphenyl)cyclohexyl, 2,6-dimethoxyphenyl, 2-ethoxy-1-naphthyl, 4-amino-4-carboxybutyl, 1-naphthylmethyl, 1-(N-ethylaminophenyl)-n-butyl, 2-carbamoylbenzyl, 4-sulfonylbenzyl, 4-sulfinylbenzyl, 2-methylthiophenyl, 2,4-dinitrobenzyl,

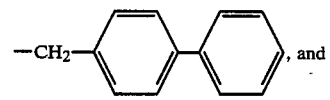, and

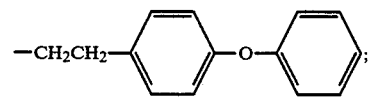;

 (c)

where $R^2$ and $R^3$ independently are:
(1) $R^1$ as previously defined;

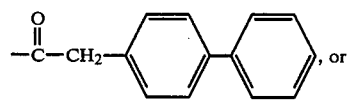 (2)

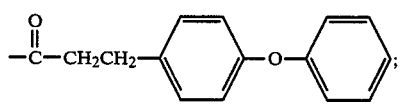;

 (3)

 (4)

-continued

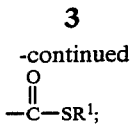 (5)

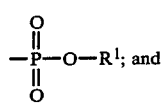 (6)

n is an integer from 1 to 4; or (d)

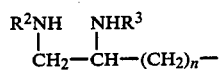

wherein $R^2$, $R^3$, and n are as defined previously;

R is
(a) hydrogen;
(b) loweralkyl, especially $C_{1-6}$ alkyl;
(c) cycloalkyl having from 3 to 8 carbon atoms; or
(d) aralkyl, such as benzyl;

Y is oxygen or methylene; and

A is a radical of
(a) myo-inositol or a configurational isomer thereof, such as scyllo-inositol and chiro-inositol, for example,

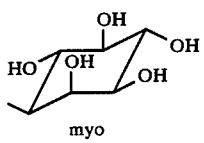 (a)

myo (b) branched chain myo-inositol, for example,

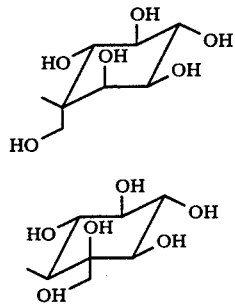 (b₁)

(b₂)

(c) 2-,4 or 5-positional isomer of myo-inositol, for example

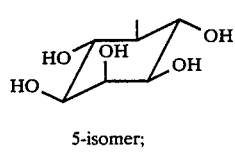 (c₁)

5-isomer;

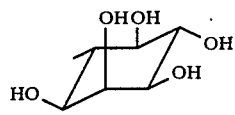 (c₂)

4-isomer;

(d) inositol substituted with a radical such as amino; azido; deoxy; halo especially fluoro or chloro; and loweralkyl especially $C_{1-6}$ alkyl such as methyl, ethyl, isopropyl, t-butyl, amyl or n-hexyl;

(e) branched-chain inositol of the structural formula

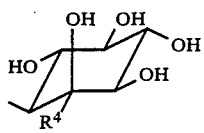 (e)

where $R^4$ is $C_{1-6}$ alkyl or substituted $C_{1-6}$ alkyl especially halomethyl such as fluoromethyl, methyl, 2-methoxyethyl, ethyl, isopropyl, t-butyl, pentyl or -methoxyhexyl;

(f) phosphoryl inositols having one or more of its hydroxy groups coupled with another

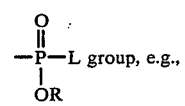 group, e.g.,

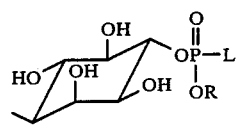

and

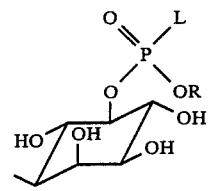

(g) epimeric myo-inositol which are linked to Y at positions configurationally opposite to those found in myo-inositol such as

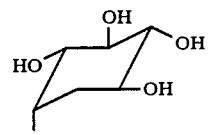

and

The preferred embodiment of this invention relates to a compound of Formula (I) wherein:

L is
(a) $R^1$; or
(b)

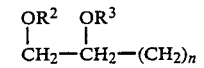

where $R^2$ and $R^3$ are as previously defined;

R is
(a) hydrogen;
(b) $C_{1-6}$ alkyl; or (c) benzyl,
Y is oxygen or methylene; and
A is a radical of
(a) myo-inositol;
(b) branched-chain myo-inositol;
(c) branched-chain inositol of formula (e);
(d) epimeric myo-inositol; or
(e) phosphonyl inositol having one or more of its hydroxy groups coupled with another

group

The most preferred embodiment of this invention relates to a compound of formula (I) wherein
L is
(a)

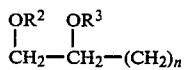

where $R^2$ and $R^3$ independently are
(1) $R^1$ where $R^1$ is $C_{7-20}$ alkyl,

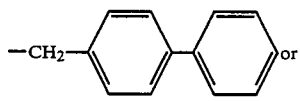

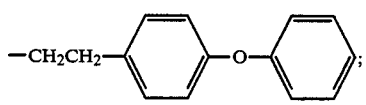

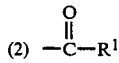

where $R^1$ is $C_{7-20}$ alkyl,

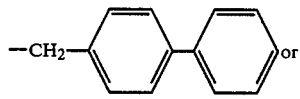

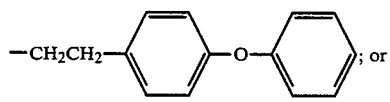

where $R^1$ is $C_{7-20}$ alkyl; or
(b) straight or branched $C_{7-20}$ alkyl especially n-octadecyl;
n is 1–2;
R is hydrogen or $C_{1-6}$ alkyl;
Y is oxygen; and
A is a radical of myo-inositol.

The novel compounds of the present invention wherein Y is O are generally prepared by a process comprising the treatment of a protected inositol derivative of formula AP' with a phosphonic or phosphorous acid derivative of formula II followed by removal of the protecting groups:

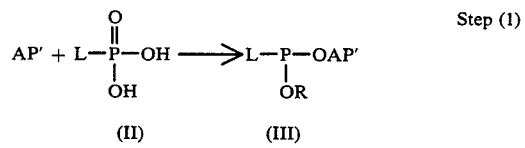

Step (1)

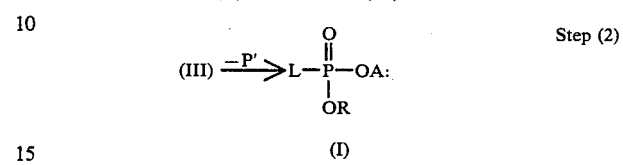

Step (2)

wherein A is an inositol radical as previously defined; and P' is a protecting group for —OH, especially unsubstituted or substituted benzyl such as benzyl, p-methoxybenzyl, m or p-nitrobenzyl, p-carboxymethylbenzyl, m-fluorobenzyl, o,p-dichlorobenzyl and p-methylthiobenzyl; and substituted or unsubstituted alkylidene especially $C_{1-6}$ alkylidene, for example, methylene, ethylidene, dimethylene, isopropylidene, cyclopentylidene, cyclohexylidene, or =CH-aryl such as

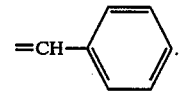

Concerning Step (1), a mixture of a protected inositol derivative, AP', and a phosphonic or phosphorous acid of formula (II) is stirred in a sufficient amount of an organic base such as pyridine, collidine, or toluidine in the presence of a condensing reagent including substituted or unsubstituted benzene sulfonylchloride, e.g., 2,4,6-triisopropylbenzenesulfonyl chloride; and trichloroacetonitrile. The reaction is usually maintained at temperatures ranging from about 25° C. to about 150° C., preferably from about 50° C. to about 80° C. Under optimum conditions, the reaction is substantially complete in about 1 hour to about 48 hours.

The resulting product from step (1) is subsequently deblocked to afford the novel compounds of this invention. Two procedures are generally applied. One for (A) the removal of benzyl protecting groups, the other (B) the removal of alkylidene protecting groups:

(A) Where P' is substituted or unsubstituted benzyl:

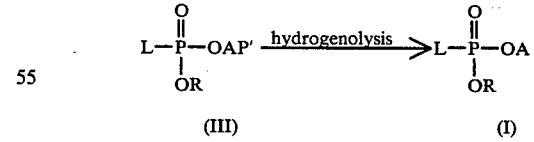

(B) Where P' is alkylidene, e.g., cyclohexylidene

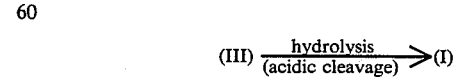

In procedure (A), an acidic solution of a benzyl protected precursor of compound (I) is treated with hydrogen in the presence of a palladium catalyst such as palladium oxide (PdO). The acidic medium used for the hydrogenolysis is usually an organic acid, for example, acetic acid, propionic acid or other $C_{1-6}$ alkanoic acids with or without a solvent such as water; $C_{1-6}$ alcohol e.g., methanol, ethanol or isopropyl alcohol; $C_{1-6}$ alkyl ester, e.g., ethyl acetate; and $diC_{1-6}$ alkyl ether, e.g., diethyl ether. Other hydrogenolysis procedures well known in the art may also be employed.

With respect to procedure (B), the alkylidene protected precursor of compound (I) is hydrolyzed in an acidic aqueous solution containing an acid such as a $C_{1-6}$ alkanoic acid especially acetic acid, propionic acid; hydrochloric acid; sulfonic or sulfuric acid. Optionally, a solubilizing solvent may be added to homogenize the reaction mixture. This solvent, for example, can be a $C_{1-4}$ alkanol such as methanol, ethanol, isopropyl alcohol or n-butanol; a ketone such as acetone, or an ether such as dioxane, or tetrahydrofuran. Heating may be required to complete the hydrolysis. Preferably, the hydrolysis is carried out in a mixture of acetic acid and water at about 40° to about 100° C. until the reaction is substantially complete.

Another group of the novel compounds of the present invention wherein Y is methylene may be prepared by a slightly different process, for example, according to the following scheme:

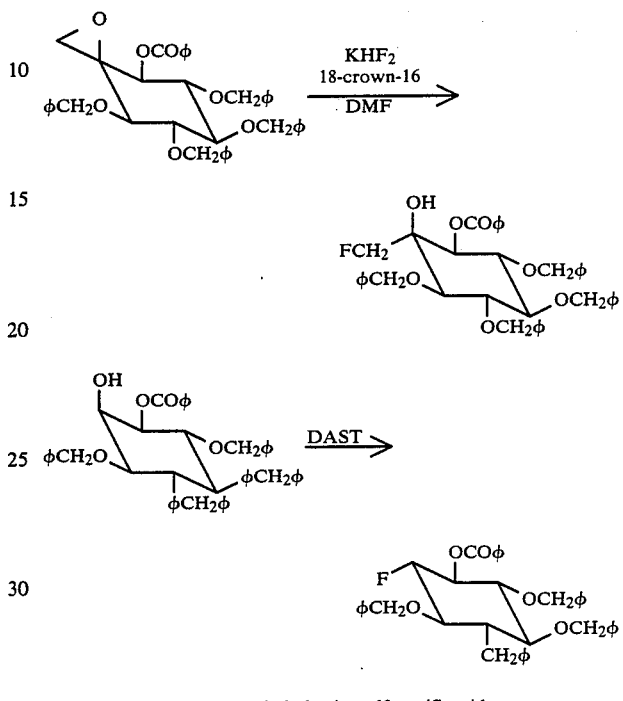

The above process is further exemplified in Example 24.

Most of the starting materials of the processes described above are commercially available or known in the literature. A few new fluoro derivatives of inositols, for example, D,L-1-O-benzoyl-2C-fluoromethyl-3,4,5,6-tetra-O-benzyl-myo-inositol and 1-O-benzoyl-2-fluoro-2-deoxy-3,4,5,6-tetra-O-benzyl-scyllo-inositol are prepared according to the following scheme:

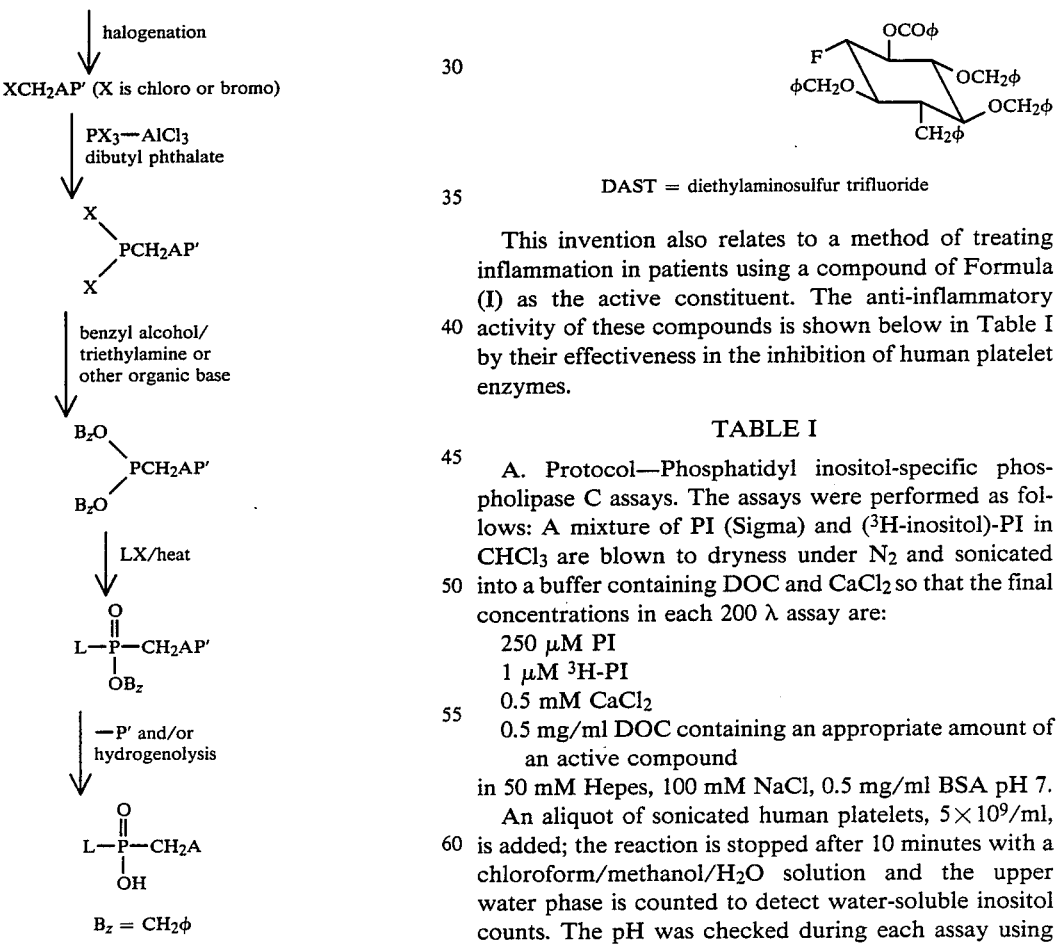

DAST = diethylaminosulfur trifluoride

This invention also relates to a method of treating inflammation in patients using a compound of Formula (I) as the active constituent. The anti-inflammatory activity of these compounds is shown below in Table I by their effectiveness in the inhibition of human platelet enzymes.

TABLE I

A. Protocol—Phosphatidyl inositol-specific phospholipase C assays. The assays were performed as follows: A mixture of PI (Sigma) and ($^3$H-inositol)-PI in CHCl$_3$ are blown to dryness under N$_2$ and sonicated into a buffer containing DOC and CaCl$_2$ so that the final concentrations in each 200 λ assay are:

250 μM PI
1 μM $^3$H-PI
0.5 mM CaCl$_2$
0.5 mg/ml DOC containing an appropriate amount of an active compound
in 50 mM Hepes, 100 mM NaCl, 0.5 mg/ml BSA pH 7.

An aliquot of sonicated human platelets, $5 \times 10^9$/ml, is added; the reaction is stopped after 10 minutes with a chloroform/methanol/H$_2$O solution and the upper water phase is counted to detect water-soluble inositol counts. The pH was checked during each assay using pH paper to verify that none of the compounds affected this parameter.

B. Results: Specific phospholipase C inhibition as shown below in Tables I and II:

TABLE I

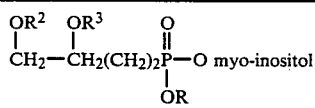

$CH_2-CH_2(CH_2)_2P-O$ myo-inositol

| Structure | | | Conc. | % Inhibition |
|---|---|---|---|---|
| $R_2$ | $R_3$ | R | | |
| n-$C_7H_{15}$CO (M) | $R_2$ | H | 1.0 mM | 64 |
| n-$C_9H_{19}$CO (N) | $R^2$ | H | 1.0 mM | 68 |
| n-$C_{15}H_{31}$CO (P) | $R^2$ | H | 1.0 mM | 84 |
| | | | 0.5 mM | 82 |
| | | | 0.05 mM | 37 |
| $\emptyset O\emptyset CH_2CH_2CO$ | (N) | H | 1.0 mM | 76 |
| | | | 0.5 mM | 66 |
| | | | 0.1 mM | 47 |
| $\emptyset-\emptyset CH_2CO$ | (N) | H | 1.0 mM | 75 |
| | | | 0.5 mM | 61 |
| (M) | (M) | $CH_3$ | 1.0 mM | 72 |
| | | | 0.5 mM | 50 |

TABLE II

| Compound | Concentration | % Inhibition |
|---|---|---|
| 1,4-di-O—(dodecylphosphonyl)-myo-inositol (example 20) | 0.043 mM | 20 |
| | 0.432 mM | 64 |
| 1-O—(octadecylphosphonyl)-myo-inositol (example 5) | 0.105 mM | 12 |
| | 1.05 mM | 66 |
| 5-O—(octadecylphosphonyl)-myo-inositol | 0.050 mM | 27 |
| | 0.20 mM | 60 |
| | 1.00 mM | 81 |
| 1,4-di(octadecylphosphonyl)-myo-inositol | 0.033 mM | 18 |
| | 0.33 mM | 37 |
| DL-2-C—hydroxymethyl-1-O—octadecanephosphonyl-myo-inositol | 0.115 mM | 51 |
| | 1.15 mM | 89 |
| 1-O—(dodecylphosphonyl)-myo-inositol | 0.20 mM | 51 |
| | 2.0 mM | 82 |
| DL-2-O—methyl-1-O—(octadecyl-phosphonyl)-myo-inositol | 0.122 mM | 53 |
| | 1.22 mM | 83 |

Accordingly, the compounds of Formula (I) of the present invention can be used to reduce inflammation and relieve pain in diseases such as emphysema, rheumatoid arthritis, osteoarthritis, gout, bronchial inflammation, infectious arthritis, rheumatic fever and the like.

For treatment of inflammation, fever or pain, the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Formulations for oral use include tablets which contain the active ingredient in admixture with non-toxic pharmaceutically acceptable excipients. These excipients may be, for example, inert diluents, such as calcium carbonate, sodium carbonate, lactose, calcium phosphate or sodium phosphate; granulating and disintegrating agents, for example, maize starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions usually contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ethyl, n-propyl, or p-hydroxybenzoate; one or more coloring agents; one or more flavoring agents; and one or more sweetening agents such as sucrose or saccharin.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may be a sterile injectable solution or suspension in a non-toxic parenterally-acceptable diluent or solvent. Among the acceptable vehicles and solvents that may be employed are water, 1,3-butanediol, Ringer's solution and isotonic sodium chloride solution. In addition, sterile fixed oils are conventionally employed as a solvent or suspending medium. For this purpose any bland fixed oil may be employed including synthetic mono- or diglycerides. Fatty acids such as oleic acid also find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug, for example, cocoa butter and polyethylene glycols.

For topical use, creams, ointments, jellies, solutions, suspensions or the like containing the anti-inflammatory agents are employed according to methods recognized in the art.

Dosage levels of the order from 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day). Preferably, a dosage of from about 2 mg to about 20 mg per kilogram of body weight per day is use to produce effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general heath, sex, diet, time of administration, route of administration, rate of excretion, drug combination and the severity of the particular disease undergoing therapy.

EXAMPLE 1

1-O-(3,4-Dipalmitoyloxybutylphosphonyl)-scylloinositol

Step A: Preparation of DL-1-O-benzoyl-2,3,4,5-tetra-O-benzylscylloinositol (2)

To a solution of DL-1-O-benzoyl-3,4,5,6-tetra-O-benzyl-myoinosose-2(1) (600 mg) in dioxane (50 ml) and methanol (40 ml) at 0° to 5° was added sodium borohydride (120 mg) in four portions over 15 minutes. The mixture was stirred at 0° to 5° for 1 hour, quenched with a few drops of acetic acid in the cold, and concentrated in vacuo to dryness. The residue was purified via preparative TLC using 1500 μm silica gel plates developed twice with 5% acetone in toluene. The slow moving Rf product was further purified in the same manner to give 300 mg of the desired product 2 (50% yield): mp 139°–140.5°.

Anal. Calcd. for $C_{41}H_{40}O_7 \cdot \frac{3}{4}H_2O$: C, 74.80; H, 6.36. Found: C, 74.86; H, 6.23.

Step B: Preparation of 1,2,3,4-tetra-O-benzylscylloinositol (3)

To a solution of DL-1-O-benzoyl-2,3,4,5-tetra-O-benzylscylloinositol (2) (1.2 g) in tetrahydrofuran (60 ml) and methanol (30 ml) was added 2.5N NaOH (6.0 ml) dropwise with stirring. The mixture was stirred at room temperature for 1 hour and evaporated to dryness. The crude product was taken up in chloroform and then recrystallized from hexane-ethanol to afford 0.80 g of 3 (79% yield): mp 178.5°–180°.

Anal. Calcd. for $C_{34}H_{36}O_6$: C, 75.53; H, 6.71. Found: C, 75.53; H, 6.93.

Step C: Preparation of DL-1-O-(3,4-dipalmitoyloxybutylphosphonyl)-2,3,4,5-tetra-O-benzylscylloinositol (4)

A mixture of 1,2,3,4-tetra-O-benzylscylloinositol (3) (270 mg), 3,4-dipalmitoyloxybutylphosphonic acid (351 mg) and triisopropylbenzene sulfonyl chloride (0.6 g) in dry pyridine (15 ml) is stirred at 70°–75° for 2½ hours, cooled to room temperature, quenched with water (0.5 ml) and concentrated in vacuo to dryness. The residue is purified via preparative TLC using 2000 μm silica gel plates developed with 12% methanol in chloroform. The purified product is recrystallized from chloroform-ethanol to give 4.

Step D: Preparation of 1-O-(3,4-dipalmitoyloxybutylphosphonyl)-scylloinositol (5)

A solution of DL-1-O-(3,4-dipalmitoyloxybutylphosphonyl)-2,3,4,5-tetra-O-benzylscylloinositol (4) (250 mg) in glacial acetic acid (100 ml) is hydrogenated over palladium black (250 mg) at atmospheric hydrogen for 3 hours and filtered through a pad of celite. The filtrate is concentrated in vacuo and the residue recrystallized from 90% aqueous acetic acid to give 1-O-(3,4-dipalmitoyloxybutylphosphonyl)-scylloinositol (5).

EXAMPLE 2

DL-1-O-(3,4-Dipalmitoyloxybutylphosphonyl)-2-O-methylmyoinositol (10)

Step A: Preparation of DL-2-O-methyl-1-O-tosyl-3,4,5,6-tetra-O-benzylmyoinositol (7)

To a solution of DL-1-O-tosyl-3,4,5,6-tetra-O-benzylmyoinositol (6) (6.95 g) and methyl iodide (10 ml) in toluene (50 ml) was added potassium hydroxide (flaked, 7.0 g) and the mixture stirred at room temperature for 1 hour. Powdered potassium hydroxide (7.0 g) was then added and the mixture was stirred for another 2.5 hours. The mixture was filtered and the filtrate evaporated to dryness. The residue was triturated with hexane. The solid product was collected and recrystallized from 5% ethyl acetate in hexane to give 6.1 g of crystalline 7 (85% yield): mp 130.5°–132°.

Anal. Calcd. for $C_{42}H_{44}O_8S$: C, 71.16; H, 6.26; S, 4.52. Found: C, 71.25; H, 6.21; S, 4.87

Step B: Preparation of DL-2-O-methyl-3,4,5,6-tetra-O-benzylmyoinositol (8)

To a solution of DL-2-O-methyl-1-O-tosyl-3,4,5,6-tetra-O-benzylmyoinositiol (7) in dry tetrahydrofuran was added lithium aluminum hydride (5.6 g) in portions and then heated to reflux for 17 hours. Additional lithium aluminum hydride (3.3 g) was charged, and the refluxing was continued for another 20 hours. The reaction mixture was cooled to room temperature, quenched carefully with ethyl acetate (ca. 40 ml), and then saturated sodium sulfate until all of the solid turned white. The mixture was filtered, and the filtrate evaporated to dryness. The residue was purified via a short silica gel column chromatography eluting with 2.5% to 5% ethyl acetate in hexane. The purified product was recrystallized from hexane-ethanol to give 2.05 g of crystalline 8 (61% yield): mp 124.5°–126°.

Anal. Calcd. for $C_{35}H_{38}O_6$: C, 75.79; H, 6.91. Found: C, 75.79; H, 6.98.

Direct monomethylation of DL-3,4,5,6-tetra-O-benzylmyoinositol with one equivalent methyl iodide and potassium hydroxide in toluene at 80° afforded 8 in 8% yield.

Step C: Preparation of DL-1-O-(3,4-dipalmitoyloxybutylphosphonyl)-2-O-methyl-3,4,5,6-tetra-O-benzylmyoinositol (9)

A mixture of DL-2-O-methyl-3,4,5,6-tetra-O-benzylmyoinositol (8) (277 mg), 3,4-dipalmitoyloxybutylphosphonic acid (351 mg) and triisopropylbenzenesulfonylchloride (0.6 g) in dry pyridine (15 ml) was stirred at 70°–75° for 3 hours, cooled to room temperature, quenched with water (0.5 ml) and concentrated in vacuo to dryness. The residue was purified via preparative TLC using 2000 μm silica gel plates developed with 10% methanol in chloroform to give the purified product 9.

Step D: Preparation of DL-1-O-(3,4-dipalmitoyloxybutylphosphonyl)-2-O-methylmyoinositol (10)

A solution of DL-1-O-(3,4-dipalmitoyloxybutylphosphonyl)-2-O-methyl-3,4,5,6-tetra-O-benzylmyoinositol (9) (150 mg) in glacial acetic acid (60 ml) is hydrogenated over palladium black (150 mg) at atmospheric hydrogen for 3 hours and filtered. The filtrate is concentrated in vacuo and the residue recrystallized from 80% aqueous acetic acid to give DL-1-O-(3,4-dipalmitoyloxybutylphosphonyl)-2-O-methylmyoinositol (10).

EXAMPLE 3

DL-1-O-(3,4-Dipalmitoyloxybutylphosphonyl)-2-C-methylmyoinositol (14)

Step A: Preparation of DL-2-C-methyl-3,4,5,6-tetra-O-benzylmyoinositol (12)

To a stirred solution of DL-1-O-benzoyl-2-oxiranyl-3,4,5,6-tetra-O-benzylmyoinositol (11) (801 mg) in tetrahydrofuran (60 ml) under nitrogen at 0° to 5° was added lithium aluminum hydride (500 mg) in portions over 20 minutes. The reaction mixture was stirred at 0° to 5° for 1 hour, at room temperature for 2 hours, and then quenched carefully with ethyl acetate first and saturated sodium sulfate until all of the solid turned white. After the filtration, the filtrate was evaporated to dryness in vacuo. The crude product was recrystallized from methanol and then from 10% acetone in hexane to afford 470 mg of crystalline 12 (59% yield): mp 118°–120°.

Anal. Calcd. for $C_{35}H_{38}O_6$: C, 75.79; H, 6.91. Found: C, 75.81; H, 7.01.

Step B: Preparation of DL-1-O-(3,4-dipalmitoyloxybutylphosphonyl)-2-C-methyl-3,4,5,6-tetra-O-benzylmyoinositol (13)

Following substantially the same procedure of Example 2, Step C, but substituting for DL-2-O-methyl-3,4,5,6-tetra-O-benzylmyoinositol (8) used therein, DL-2-C-methyl-3,4,5,6-tetra-O-benzylmyoinositol (12), there is obtained DL-1-O-(3,4-dipalmitoyloxybutylphosphonyl)-2-C-methyl-3,4,5,6-tetra-O-benzylmyoinositol (13).

Step C: Preparation of DL-1-O-(3,4-dipalmitoyloxybutylphosphonyl)-2-C-methylmyoinositol (14)

Following the procedure of Example 2, Step D, but substituting for DL-1-O-(3,4-dipalmitoyloxybutylphosphonyl)-2-O-methyl-3,4,5,6-tetra-O-benzylmyoinositol (9) used therein, DL-1-O-(3,4-dipalmitoyloxybutylphosphonyl)-2-C-methyl-3,4,5,6-tetra-O-benzylmyoinositol (13), there is obtained DL-1-O-(3,4-dipalmitoyloxybutylphosphonyl)-2-C-methylmyoinositol (14).

EXAMPLE 4

DL-6-Deoxy-1-O-(3,4-dipalmitoyloxybutylphosphonyl)-chiroinositol (19)

Step A: Preparation of DL-3,4,5,6-tetra-O-benzyl-1-O-trifluoromethanesulfonylmyoinositol (16)

To a stirred solution of DL-1,4,5,6-tetra-O-benzylmyoinositol (15) (1.08 g) in dry methylene chloride (25 ml) containing dry pyridine (1.0 ml) at −15° to −20° under nitrogen was added a solution of trifluoromethanesulfonic anhydride (0.38 ml) in methylene chloride (3 ml) over 15 minutes. The mixture was stirred at −15° for 1 hour, at 0° for 0.5 hour and then at room temperature for 0.5 hour before quenched with cold 5% sodium bicarbonate solution. The organic phase was washed with water, brine and dried ($Na_2SO_4$). Removal of solvent gave the crude product which was purified by passing through a short silica gel column with 50% ethyl acetate in hexane. Subsequent recrystallization from 5% ethyl acetate in hexane afforded 1.08 g of crystalline 16 (80% yield): mp 112°–113° (dec.).

Anal. Calcd. for $C_{35}H_{35}F_3O_8S$: C, 62.49; H, 5.24; F, 8.47; S, 4.77. Found: C, 62.85; H, 5.26; F, 8.60; S, 4.98.

Step B: Preparation of DL-1-deoxy-3,4,5,6-tetra-O-benzylmyoinositol (17) [DL-6-deoxy-2,3,4,5-tetra-O-benzylchiroinositol]

To a solution of DL-3,4,5,6-tetra-O-benzyl-1-O-trifluoromethanesulfonylmyoinositol (16) (202 mg) in dry tetrahydrofuran (15 ml) under nitrogen at room temperature was added a solution of 1.2M lithium triethyl hydridoborate (1.0 ml). The mixture was stirred at room temperature for 1 hour, quenched with excess ethyl acetate and evaporated to dryness. The residue was treated with water (5 ml) and extracted with chloroform (10 ml×3). The organic solution was dried ($Na_2SO_4$), concentrated and the crude product purified via preparative TLC using 2000 μm silica gel plates developed with 33% ethyl acetate in hexane. The product was further purified through another preparative TLC using 1000 μm silica gel plates developed first with 12% acetone in hexane and then with 16% acetone in hexane. Isolation of the more mobile product afforded 95 mg of 17 as a viscous mass: ir (nujol), 3450 cm$^{-1}$; 60 MHzNMR (CDCl$_3$)δ 2.33 (dt. 2H, J=14.0, 4.2 Hz, C-1 methylene), 2.47 (s, 1H C-2 OH), 3.2–4.2 (m, 5H, 5X CH—O), 4.71 (s, 4H, 2 X $CH_2C_6H_5$), 4.85 (s, 2H, $C\underline{H}_2C_6H_5$), 4.89 (s, 2H, $C\underline{H}_2C_6H_5$) and 7.3 ppm (s, 20 H, 4 X $C_6H_5$).

Anal.: Calcd. for $C_{34}H_{36}O_5 \cdot \frac{1}{2}H_2O$: C, 76.52; H, 7.00. Found: C, 76.69; H, 6.81.

Step C: Preparation of DL-6-deoxy-1-O-(3,4-dipalmitoyloxybutylphosphonyl)-2,3,4,5-tetra-O-benzylchiroinositol (18)

Following the procedure of Example 2, Step C, but substituting for the DL-2-O-methyl-3,4,5,6-tetra-O-benzylmyoinositol (8) used therein, an equivalent amount of DL-6-deoxy-2,3,4,5-tetra-O-benzylchiroinositol (17), there is prepared DL-6-deoxy-1-O-(3,4-dipalmitoyloxybutylphosphonyl)-2,3,4,5-tetra-O-benzylchiroinositol (18).

Step D: Preparation of DL-6-deoxy-1-O-(3,4-dipalmitoyloxybutylphosphonyl)-chiroinositol (19)

Following the procedure of Example 2, Step D, but substituting for the DL-1-O-(3,4-dipalmitoyloxybutylphosphonyl)-2-O-methyl-3,4,5,6-tetra-O-benzylmyoinositol (9) used therein, an equivalent amount of DL-6-deoxy-1-O-(3,4-dipalmitoyloxybutylphosphonyl)-2,3,4,5-tetra-O-benzylchiroinositol (18), there is produced DL-6-deoxy-1-O-(3,4-dipalmitoyloxybutylphosphonyl)-chiroinositol (19).

EXAMPLE 5

1-O-Octadecylphosphonyl-scylloinositol

Step A: Preparation of 1-O-(octadecylphosphonyl)-2,3,4,5-tetra-O-benzylscylloinositol (A)

To a stirred solution of 1,2,3,4-tetra-O-benzylscylloinositol (3) (541 mg) and octadecylphosphonic acid (334 mg) in dry pyridine (20 ml) at 70°–75° was added triisopropylbenzenesulfonyl chloride (1.05 g). The mixture was heated at 70°–75° for 2½ hours, cooled to room temperature, quenched with water (1.0 ml) and concentrated in vacuo to dryness. The residue was purified via preparative TLC using 2000 μm silica gel plates developed with 12% methanol in chloroform. The purified product was recrystallized from methylene chloride-ethanol to give 695 mg of A (80% yield): mp 243°–248°.

Anal. Calcd. for $C_{52}H_{73}O_8P \cdot H_2O$: C, 71.37; H, 8.64; P, 3.54. Found: C, 71.18; H, 8.36; P, 3.51.

Step B: Preparation of 1-O-octadecylphosphonylscylloinositol

A solution of 1-O-octadecylphosphonyl-2,3,4,5-tetra-O-benzylscylloinositol (A) (400 mg) in 95% aqueous acetic acid (200 ml) was hydrogenated over freshly generated palladium black (380 mg) at atmospheric hydrogen for 2½ hours. The resulting mixture was heated to 80° to 90° and filtered through a pad of celite. The filtrate was cooled in an ice-bath and the crystalline product collected and dried to afford 120 mg of 1-O-octadecylphosphonylscylloinositol (51% yield): mp 212°–217° C.

Anal. Calcd. for $C_{24}H_{49}O_8P$: C, 58.04; H, 9.95; P, 6.24. Found: C, 57.72; H, 9.97; P, 6.64.

EXAMPLE 6

2-Fluoro-2-deoxy-1-O-octadecylphosphonylscylloinositol (24)

Step A: Preparation of 1-1-benzoyl-2-fluoro-2-deoxy-3,4,5,6-tetra-O-benzylscylloinositol (21)

To a solution of DL-1-O-benzoyl-3,4,5,6-tetra-O-benzylmyoinositol (20) (2.70 g) in dry toluene (350 ml) at 65° was added under nitrogen diethylaminosulfur trifluoride (1.5 ml) during 10 minutes. The mixture was heated to 85° for 3 minutes, stirred at room temperature overnight and poured into cold 5% sodium bicarbonate solution (300 ml). The crude product was extracted with chloroform (500 ml; 200 ml). The organic extract was washed with water, brine, dried over anhydrous sodium sulfate, and evaporated in vacuo to give the crude product. It was recrystallized twice from 2% chloroform in ethanol to afford 2.33 g of pure 21 (86% yield): mp 134.5°–135.5°; 300 MHz NMR (CDCl$_3$) δ3.61 (t, 1H, J=9.4 Hz, H-5), 3.64 (t, 1H, J=9.0 Hz, H-4), 3.67 (t, 1H, J=9.5 Hz, H-6), 3.82 (dt, 1H, J=13.0, 9.2 Hz, H-3), 4.62 (dt, 1H, J=51, 9.2 Hz, H-5) and 5.55 ppm (dt, J=13.0, 9.5 Hz, H-1).

Anal. Calcd. for $C_{41}H_{39}O_6F$: C, 76.14; H, 6.08; F, 2.94 Found: C, 76.43; H, 6.13; F, 2.88.

Following substantially the same procedure, the following compounds also prepared were:

| Name | Physical properties |
| --- | --- |
| DL-1-O—benzyl-2-C—bromomethyl 2-fluoro-2-deoxy-3,4,5,6-tetra-O—benzylmyoinositol (1a) | m.p. 181.0–183.5°; Anal. Calcd for $C_{42}H_{40}BrFO_6$: C, 68.20; H, 5.45; Br, 10.80; F, 2.57. Found: C, 68.29; H, 5.27; Br, 10.97; F, 2.71. |
| DL-2-C—acetoxymethyl-1-O—benzoyl-2-fluoro-2-deoxy-3,4,5,6-tetra-O—benzylmyoinositol (2a) | m.p. 168.0–169.5°; Anal. Calcd for $C_{44}H_{43}FO_8$: C, 73.52; H, 6.03; F, 2.64. Found: C, 73.82; |

-continued

| Name | Physical properties |
|------|---------------------|
| DL-1-fluoro-1-deoxy-6-oxiranyl-2,3,4,5-tetra-O—benzylchiroinositol (3a) | H, 6.04; F, 2.71. m.p. 132–133°; Anal. Calcd for $C_{35}H_{35}FO_5$: C, 75.79; H, 6.36; F, 3.43. Found: C, 75.51; H, 6.37; F, 3.32. |
| 1-O—acetyl-2-fluoro-2-deoxy-2-C—methyl-3,4,5,6-tetra-O—benzylscylloinositol (4a) | mass m/e 598, 507 ($M^+$ —$CH_2C_6H_5$); 300 MHz NMR ($CDCl_3$): δ 1.44 (d, $J$ = 23Hz, $CH_3$—CF), 5.30 (dd, $J$ = 13, 10 Hz, H-1), 3.78 (dd, $J$ = 13, 10 Hz, H-3). |
| DL-1-O—benzoyl-2-fluoro-2-deoxy-3,4,5,6-tetra-O—benzylmyoinositol (5a) | mass m/e 646, 555 ($M^+$ —$CH_2C_6H_5$); 300 MHz NMR ($CDCl_3$): δ 3.65 (ddd, $J$ = 28, 10 2.5 Hz, H-3), 5.12 (dt, $J$ = 52, 2.5 Hz, H-2), 5.14 (ddd, $J$ = 28, 10, 2.5 Hz, H-1). |
| DL-2-O—benzoyl-1-fluoro-1-deoxy-3,4,5,6-tetra-O—benzylmyoinositol (6a) | mass m/e 646, 555 ($M^+$ —$CH_2C_6H_5$); 300 MHz NMR ($CDCl_3$): δ 4.72 (ddd, $J$ = 50, 5, 2 Hz, H-1), 5.45 (dt, $J$ = 10, 4 Hz, H-2). |
| DL-6-O—benzoyl-1-fluoro-1-deoxy-2,3,4,5,-tetra-O—benzylchiroinositol (7a) | mass m/e 646, 555 ($M^+$ —$CH_2C_6H_5$); 300 MHz NMR ($CDCl_3$): δ 3.86 (ddd, $J$ = 31, 10, 3 Hz, H-2), 4.84 (ddd, $J$ = 51, 1, 4.2 Hz, H-1), 5.81 (dt, $J$ = 4.5, 3 Hz, H-6). |

Step B: Preparation of 2-fluoro-2-deoxy-3,4,5,6-tetra-O-benzylscylloinositol (22)

A solution of 1-O-benzoyl-2-fluoro-2-deoxy-3,4,5,6-tetra-O-benzylscylloinositol (21) (1.0 g) in tetrahydrofuran (50 ml) and methanol (25 ml) was stirred under nitrogen in the presence of 20% sodium hydroxide (3.0 ml) for 2 hours. The reaction mixture was diluted with water (50 ml), concentrated in vacuo to remove most of the organic solvents, and then extracted with chloroform (50 ml×2). The pooled organic extracts were washed with water and brine, dried over anhydrous sodium sulfate and concentrated in vacuo to give the crude product. It was recrystallized from ethanol-hexane to give 0.80 g of pure 22 (98% yield): mp 113.5°–114.5°; 300 MHz NMR ($CDCl_3$) δ3.40 (t, 1H, J=9.5 Hz, H-5), 3.57 (t, 2H, J=9 Hz, H-4 and H-6), 3.57 (dt, 1H, J=13.0, 9 Hz, H-3), 3.74 (dtd, 1H, J=13.0, 9, 2 Hz, H-1), and 4.42 ppm (dt, 1H, J=52, 9 Hz, H-2).

Anal. Calcd. for $C_{34}H_{35}FO_5$ C, 75.25; H, 6.50; F, 3.50 Found: C, 75.34; H, 6.53; F, 3.84.

Following substantially the same procedure, the following compounds were also prepared:

| Name | Physical properties |
|------|---------------------|
| DL-2-C—bromomethyl-2-fluoro-2-deoxy-3,4,5,6-tetra-O—benzylmyoinositol (8a) | m.p. 115.5–116°; Anal. Calcd for $C_{35}H_{36}BrFO_5$: C, 66.14; H, 5.71; Br, 12.57; F, 2.99. Found: C, 66.81; H, 5.44; Br, 12.98; F, 2.84. |
| DL-2-fluoro-2-deoxy-2-C—hydroxymethyl-3,4,5,6-tetra-O—benzylmyoinositol (9a) | m.p. 141.5–142.5°; mass m/e 572, 481 ($M^+$ —$CH_2C_6H_5$). |
| DL-2-fluoro-2-deoxy-3,4,5,6-tetra-O—benzylmyoinositol (10a) | mass m/e 542, 451 ($M^+$ —$CH_2C_6H_5$); 300 MHz NMR ($C_6D_6$): δ 3.13 (ddd, $J$ = 29, 9, 2 Hz, H-3), 3.15 (dddd, $J$ = 29, 9, 5, 2 Hz, H-1), 4.80 (dt, $J$ = 52, 2 Hz, H-2). |
| DL-1-fluoro-1-deoxy-3,4,5,6-tetra-O—benzylmyoinositol (11a) | mass m/e 542, 451 ($M^+$—$CH_2\emptyset$); 300 MHz NMR ($CDCl_3$): δ 4.65 (ddd, $J$ = 50, 5, 2 Hz, H-1). |
| DL-1-fluoro-1-deoxy-2,3,4,5-tetra-O—benzylchiroinsoitol (12a) | mass m/e 542, 451 ($M^+$—$CH_2\emptyset$); 300 MHz NMR ($CDCl_3$): δ 4.22 (dt, $J$ = 4, 3 Hz, H-6), 4.94 (ddd, $J$ = 47, 5, 2 Hz, H-1). |

Step C: Preparation of 2-fluoro-2-deoxy-1-O-octadecylphosphonyl-3,4,5,6-tetra-O-benzylscylloinositol (23)

Following the procedure of Example 5, Step A, but substituting for the 1,2,3,4-tetra-O-benzylscylloinositol (3) used therein, an equivalent amount of 2-fluoro-2-deoxy-3,4,5,6-tetra-O-benzylscylloinositol (22), there is produced 2-fluoro-2-deoxy-1-O-octadecylphosphonyl-3,4,5,6-tetra-O-benzylscylloinositol (23).

Step D: Preparation of 2-fluoro-2-deoxy-1-O-octadecylphosphonylscylloinositol (24)

Following the procedure of Example 5, Step B, but substituting for the 1-O-octadecylphosphonyl-2,3,4,5-tetra-O-benzylscylloinositol (A) used therein, an equivalent amount of 2-fluoro-2-deoxy-1-O-octadecyl-phosphonyl-3,4,5,6-tetra-O-benzylscylloinositol (23), there is prepared 2-fluoro-2-deoxy-1-O-octadecylphosphonylscylloinositol (24).

EXAMPLE 7

3,4-Dipalmitoyloxybutyl-1-phosphonyl-myo-inositol

Step A: Preparation of 3,4-dipalmitoyloxybutyl-1-phosphonyl-(2,3,4,5,6-penta-O-benzyl-myo-inositol)

To a solution of 3,4-dipalmitoyloxybutyl-1-phosphonic acid [prepared by the process set forth in J. C. Tang et al., Chem. Phys. Lipids. 17; 169 (1976)] (500 mg, 0.77 mmol) and 2,3,4,5,6-penta-O-benzyl-myo-inositol [prepared by the process set forth in R. Gigg and C. D. Warren, J. Chem. Soc. (C), 2367 (1969)](731 mg, 1.16 mmol) in pyridine, (18 ml) was added trichloroacetonitrile (2.5 ml, 24.9 mmol). The mixture was stirred at 60° for 24 hours, and the product was precipitated by addition of acetonitrile (30 ml). The solid was filtered, washed with acetonitrile followed by dissolution in a small volume of chloroform. The resulting solution was applied to a column of silica gel (Merck No. 7734) and eluted initially with chloroform and then successively with 50:1, 40:1, and finally 30:1 chloroform-methanol. 3,4-Dipalmitoyloxybutyl-1-phosphonyl-(2,3,4,5,6-penta-O-benzyl-myo-inositol) was obtained as a colorless syrup resulting from combination and evaporation of the appropriate fractions; yield 394 mg (40%). 300 MHz nmr spectrum (CDCl$_3$: δ0.88 [t, (CH$_2$)$_{14}$CH$_3$]; 1.23 [m, (CH$_2$)$_{13}$]; and 7.23 (broad m, phenyl).

Step B: Preparation of 3,4-dipalmitoyloxybutyl-1-phosphonyl-myo-inositol

A solution of 3,4-dipalmitoyloxybutyl-1-phosphonyl-(2,3,4,5,6-penta-O-benzyl-myo-inositol) (326 mg, 0.26 mmol) in glacial acetic acid (20 ml) was hydrogenolyzed in the presence of palladium, added in the form of PdO (1 g), at room temperature for 48 hours. The reaction mixture was filtered through celite, the residue washed with acetic acid and subsequently with 40:10:1 chloroform-methanol:water until thin-layer chromatographic investigation indicated complete extraction of product from the catalyst. The combined filtrates were evaporated and then coevaporated several times with toluene. The residue was taken up in a small volume of 40:10:1 chloroform-methanol-water and applied to a silica gel column (Merck No. 7734, packed as a slurry in chloroform). Elution was effected with chloroform initially, then with 9:1 chloroform-methanol, 90:10:1, 40:10:1, and finally 70:30:3 chloroform-methanol-water. The fractions containing the desired product were combined and evaporated to afford 3,4-dipalmitoyloxybutyl-1-phosphonyl-myo-inositol as a white solid, yield 165 mg (79%). 300 MHz nmr spectrum (DMSO-d$_6$): δ0.85 [t, (CH$_2$)$_{14}$CH$_3$] and 1.22 [broad s, (CH$_2$)$_{13}$].

EXAMPLE 8

Preparation of 3,4-Didecanoyloxybutyl-1-phosphonyl-myo-inositol

Step A: Preparation of 3,4-didecanoyloxybutyl-1-bromide

To a solution of 3,4-dihydroxybutyl-1-bromide [prepared by the process set forth in J. C. Tang et al., *Chem. Phys. Lipids*, 17, 169 (1976)] (1.5 g, 8.9 mmol) in dichloromethane (50 ml) were added pyridine (3 ml) and 4-dimethylaminopyridine (200 mg). The solution was cooled in an ice-bath, and a solution of decanoic anhydride (5.7 g, 17.5 mmol) in dichloromethane was added. The reaction mixture was stirred for 1 hour in an ice-bath and then overnight at room temperature. The mixture was poured into ice-water, the organic layer separated, the aqueous layer extracted with dichloromethane, the combined organic extracts washed with 2.5N hydrochloric acid, saturated sodium hydrogencarbonate solution, water, and evaporated. The residue was chromatographed on a column of silica gel (Merck No. 7734) and was eluted with 1:10 diethyl ether-hexane. 3,4-didecanoyloxybutyl-1-bromide was obtained as an oil, yield 1.8 g (43%). 60 MHz nmr spectrum (CDCl$_3$): δ0.89 [t, (CH$_2$)$_8$CH$_3$]; 1.29 [broad s, (CH$_2$)$_7$]; 3.42 (m, CH$_2$Br); 3.92–4.49 (m, 2H, H-4); and 5.07–5.43 (m, 1H, H-3).

Step B: Preparation of 3,4-didecanoyloxybutyl-1-phosphonic acid

A mixture of 3,4-didecanoyloxybutyl-1-bromide (1.5 g, 3.1 mmol) and tris(trimethylsilyl)phosphite (5.2 ml, 15.7 mmol) was stirred at 195° under nitrogen overnight. Excess phosphite was removed by vacuum distillation (110°, 1 torr). To the residue was added water (1.6 ml) and tetrahydrofuran (14.4 ml), and the mixture was heated at reflux for 2 hours. The reaction mixture was filtered through celite, the filtrate evaporated and coevaporated several times with methanol and toluene. The resulting phosphonic acid was immediately reacted with 2,3,4,5,6-penta-O-benzyl-myo-inositol as described below in Step C.

Step C: Preparation of 3,4-didecanoyloxybutyl-1-phosphonyl-(2,3,4,5,6-penta-O-benzyl-myo-inositol To a solution of the phosphonic acid obtained in Step B (500 mg, 1.04 mmol) and 2,3,4,5,6-penta-O-benzyl-myo-inositol (659 mg, 1.04 mmol) in pyridine (15 ml) was added trichloroacetonitrile (1.8 ml, 18.0 mmol). The mixture was stirred at 60° for 18 hours with exclusion of moisture, cooled, evaporated under diminished pressure and coevaporated several times with toluene. The residue was dissolved in a small volume of chloroform, and the solution was applied to a column of silica gel (Merck No. 7734) that was eluted initially with chloroform and subsequently with 50:1, 40:1, and finally 25:1 chloroform-methanol. 3,4-Didecanoyloxybutyl-1-phosphonyl-(2,3,4,5,6-penta-O-benzyl-myo-inositol) was obtained as a colorless syrup after combination and evaporation of the appropriate fractions, yield 330 mg (29%). αMHz nmr spectrum (CDCl$_3$: δ0.87 [t, (CH$_2$)$_8$CH$_3$]; 1.23 [m, (CH$_7$]; 4.67–4.83 (m, OCH$_2$Ph); and 7.13–7.27 (m, phenyl).

Step D: Preparation of 3,4-didecanoyloxybutyl-1-phosphonyl-myo-inositol

A solution of 3,4-didecanoyloxybutyl-1-phosphonyl(2,3,4,5,6-penta-O-benzyl-myo-inositol) (330 mg) in glacial acetic acid (20 ml) was hydrogenolyzed in the presence of palladium, added in the form of PdO (500 mg), at room temperature for 24 hours. The catalyst was removed by filtration through celite, and the filtrate evaporated and coevaporated several times with toluene. The residue was dissolved in a small volume of 40:10:1 chloroform methanol-water, and the solution was applied to a column of silica gel (Merck No. 7734, packed as a slurry in chloroform). Elution was effected with the following step gradients: chloroform, 9:1 chloroform-methanol, 90:10:1, 40:10:1, 70:30:3, and finally 6:4:1 chloroform-methanol-water. The syrup obtained upon evaporation of the appropriate fractions was dissolved in methanol and the solution passed through a short column of AG50W-X4 ion-exchange resin (hydrogen ion form) which had been thoroughly washed with methanol. Elution with methanol afforded pure 3,4-didecanoyloxybutyl-1-phosphonyl-myo-inositol, yield 128 mg (66%).

Anal. Calc. for C$_{30}$H$_{57}$O$_{12}$P.H$_2$O: C, 54.70; H, 9.03. Found: C, 54.83; H, 8.83.

EXAMPLE 9

3,4-Dioctanoyloxybutyl-1-phosphonyl-myo-inositol

In substantially the same manner as described in Example 8, but substituting for the 3,4-didecanoyloxybutyl-1-phosphonic acid used therein, a stoichiometric equivalent amount of 3,4-dioctanoyloxybutyl-1-phosphonic acid, there are obtained the protected phosphonate ester, 3,4-dioctanoyloxybutyl-1-phosphonyl-(2,3,4,5,6-penta-O-benzyl-myo-inositol) and subsequently the deprotected derivative, 3,4-dioctanoyloxybutyl-1-phosphonyl-myo-inositol.

EXAMPLE 10

3,4-Dihexanoyloxybutyl-1-phosphonyl-myo-inositol

In substantially the same manner, as described in Example 8, but substituting for 3,4-didecanoyloxybutyl-1-phosphonic acid used therein, a stoichiometric equivalent amount of 3,4-dihexanoyloxybutyl-1-phosphonic acid, there are obtained the protected phosphonate ester, 3,4-dihexanoyloxybutyl-1-phosphonyl-(2,3,4,5,6-penta-O-benzyl-myo-inositol) and subsequently the deprotected derivative, 3,4-dihexanoyloxybutyl-1-phosphonyl-myo-inositol.

EXAMPLE 11

3,4-Dibutyroyloxybutyl-1-phosphonyl-myo-inositol

In like manner as described in Example 8, but substituting for the 3,4-didecanoyloxybutyl-1-phosphonic acid used therein, a stoichiometric equivalent amount of 3,4-dibutyroyloxybutyl-1-phosphonic acid, there are obtained the protected phosphonate ester, 3,4-dibutyroyloxy-butyl-1-phosphonyl-(2,3,4,5,6-penta-O-benzyl-myo-inositol) and subsequently the deprotected derivative, 3,4-dibutyroyloxybutyl-1-phosphonyl-myo-inositol.

EXAMPLE 12

3,4-Diacetyloxybutyl-1-phosphonyl-myo-inositol

In like manner, as described in Example 8, but substituting for the 3,4-didecanoyloxybutyl-1-phosphonic acid used therein, a stoichiometric equivalent amount of 3,4-diacetyloxybutyl-1-phosphonic acid, there are obtained the protected phosphonate ester, 3,4-diacetyloxybutyl-1-phosphonyl-(2,3,4,5,6-penta-O-benzyl-myo-inositol) and subsequently the deprotected derivative, 3,4-diacetyloxybutyl-1-phosphonyl-myo-inositol.

EXAMPLE 13

3-Decanoyloxy-4-(p-phenoxyphenyl)-butyroyloxybutyl-1-phosphonyl-myo-inositol In like manner as described in Example 8, but substituting for 3,4-didecanoyloxybutyl-1-phosphonic acid used therein, a stoichiometric equivalent amount of 3 decanoyloxy-4-(p-phenoxyphenyl)-butyroyloxybutyl-1-phosphonic acid, there are obtained the protected phosphonate ester, 3-decanoyloxy-4-(p-phenoxyphenyl)-butyroyloxybutyl-1-phosphonyl-(2,3,4,5,6-penta-O-benzyl-myo-inositol) and subsequently the deprotected derivative, 3-deca-noyloxy-4-(p-phenoxyphenyl)-butyroyloxybutyl-1-phosphonyl-myo-inositol.

EXAMPLE 14

3-Decanoyloxy-4-(p-diphenylacetyloxy)-butyl-1-phosphonyl-myo-inositol

In like manner as described in Example 8, but substituting for 3,4-didecanoyloxybutyl-1-phosphonic acid used therein, a stoichiometric equivalent amount of 3-decanoyloxy-4-(p-diphenylacetyloxy)butyl-1-phosphonic acid, there are obtained the protected phosphonate ester, 3-decanoyl-oxy-4(p-diphenylacetyloxy)butyl-1-phosphonyl-(2,3,4,5,6)-penta-O-benzyl-myo-inositol) and subsequently the deprotected derivative, 3-decanoyloxy-4(p-diphenylacetyloxy)butyl-1-phosphonyl-myo-inositol.

EXAMPLE 15

Preparation of 3,4-Dioctadecyloxybutyl-1-phosphonyl-myo-inositol

Step A: Preparation of 3,4-dioctadecyloxybutyl-1-phosphonyl-(2,3,4,5,6-penta-O-benzyl-myo-inositol)

To a solution of 3,4-dioctadecyloxybutyl-1-phosphonic acid [prepared by the process set forth in A. F. Rosenthal, *J. Chem. Soc.*, 7345 (1965)] (200 mg, 0.30 mmol) and 2,3,4,5,6-penta-O-benzyl-myo-inositol (290 mg, 0.46 mmol) in pyridine (3 ml) was added trichloroacetonitrile (1.2 ml, 12.0 mmol). The reaction mixture was stirred at 60° for 4 hours with exclusion of moisture. Most of the pyridine was then removed by evaporation under diminished pressure. Addition of trifluoroacetic acid (0.5 ml), acetonitrile, and finally hexane gave rise to a two-phase mixture. The lower layer was discarded and the upper layer was allowed to stand at room temperature for 4 days. The solution was evaporated, the residue taken up in a small volume of chloroform, and the solution applied to a column of silica gel (Merck No. 7734) that was eluted with 20:1 chloroform-methanol. The fractions containing the desired product were combined and evaporated to a syrup that solidified upon trituration with acetonitrile. The solid was filtered and dried in vacuo to afford pure 3,4-dioctadecyloxybutyl-1-phosphonyl-(2,3,4,5,6-penta-O-benzyl-myo-inositol); yield 144 mg (38%).

Anal. Calc. for $C_{81}H_{123}O_{10}P \cdot 1.5H_2O$: C, 73.99; H, 9.66; P, 2.36. Found: C, 73.87; H, 9.71; P, 2.26.

Step B: 3,4-Dioctadecyloxybutyl-1-phosphonyl-myo-inositol

A solution of 3,4-dioctadecyloxybutyl-1-phosphonyl-(2,3,4,5,6-penta-O-benzyl-myo-inositol) (103 mg, 0.08 mmol) in glacial acetic acid (5 ml) was hydrogenolyzed in the presence of palladium, added in the form of PdO (125 mg), at room temperature for 7 days. The catalyst was removed by filtration through celite, the filter washed with 40:10:1 chloroform-methanol-water until thin-layer chromatographic investigation indicated complete extraction from the catalyst. The combined filtrates were evaporated, the residue dissolved in a small volume of chloroform, and the solution applied to a column of silica gel (Merck No. 7734) that was eluted initially with 9:1 chloroform-methanol and subsequently with 90:10:1, 40:10:1, and 70:30:3 chloroform-methanol water. The fractions containing the desired product were combined and evaporated to afford 3,4-dioctadecyloxybutyl-1-phosphonyl-myo-inositol as a white solid. 300 MHz nmr spectrum in (CDCl$_3$, CD$_3$OD, D$_2$O mixture): δ0.82 [t, O(CH$_2$)$_{17}$C$\underline{H}_3$]; 1.22 (m, C$\underline{H}_2$)$_{16}$).

EXAMPLE 16

1-(3',4'-dibutyroyloxybutylphosphonyl)-1-C-hydroxymethyl-myo-inositol

Step A: Preparation of 2,3,4,5,6-penta-O-benzyl-myo-1-inosose

Pyridinium chlorochromate (1.0 g) was added to a solution of (±)-2,3,4,5,6-penta-O-benzyl-myo-inositol (2.0 g) in dichloromethane at 25°. After stirring for 48 hours at 25°, the reaction mixture was vacuum filtered through silica gel (Merck No. 7734) eluting with diethyl ether. The filtrate was evaporated and the residue was recrystallized from methanol to give flocculent white crystals (1.2 g, 60%). M.p. 87°–89° C.

Step B: Preparation of 2,3,4,5,6-penta-O-benzyl-1-C-benzyloxymethyl-myo-inositol A solution of (benzyloxymethyl)tributylstannane (2.2 g) in tetrahydrofuran (20 ml) was cooled to −78° under a nitrogen atmosphere and n-butyllithium (3.0 ml, 1.6M in hexane) was added. After 10 minutes at −78°, 2,3,4,5,6 penta-O-benzyl-myo-1-inosose (1.5 g, 2.4 mmole) in tetrahydrofuran (5 ml) was added. After another 15 minutes at −78°, the reaction mixture was partitioned between diethyl ether and water. The phases were separated and the organic phase was dried (sodium sulfate) and evaporated. The residue was purified by high performance liquid chromatography (silica gel) to give 2,3,4,5,6-penta-O-benzyl-1-C-benzyloxymethyl-myo-inositol (0.67 g, 37%).

Anal. Calc. for $C_{49}H_{50}O_7$: C, 78.37; H, 6.71. Found: C, 78.42; H, 6.79.

Step C: Preparation of 3,4-dibutyroyloxybutyl-1-bromide

Butyric anhydride (1.6 ml) was added to a solution of 3,4-dihydroxybutyl-1-bromide [prepared by the process set forth in J. C. Tang et al., *Chem. Phys. Lipids.*, 17, 169 (1976)] (80 mg) and 4-dimethylaminopyridine (57 mg) in pyridine (3 ml) and dichloromethane (20 ml) at 0°. The reaction was stirred at 25° for 3 hours and then poured into ice-water and extracted with ether. The organic layer was washed with 1N HCl, saturated aqueous sodium hydrogen carbonate and saturated aqueous sodium chloride, dried (sodium sulfate) and evaporated. The crude product was purified by high performance liquid chromatography (silica gel) eluting with 9:1 hexane/ethyl acetate. Evaporation of the fractions containing the desired product gave 3,4-dibutyroyloxybutyl-1-bromide as a colorless oil (1.0 g, 69%). Mass spectrum (m/e) 221. ($M^+$—$CH_3(CH_2)_2CO_2$.)

Step D: Preparation of 3,4-dibutyroyloxybutyl-1-phosphonic acid

Tris(trimethylsilyl)phosphite (1.2 ml) was added to 3,4-dibutyroyloxybutyl-1-bromide (220 mg). The reaction mixture was heated for 18 hours under nitrogen at 170°. A red precipitate was formed and vigorous refluxing occurred during the course of the reaction. Excess tris(trimethylsilyl)phosphite was removed by vacuum distillation (75°, 7 torr). Water (2 ml) and tetrahydrofuran (18 ml) were added to the residue and the mixture was heated to reflux for 2 hours. The red precipitate was removed from the cooled reaction mixture by vacuum filtration through celite and the solids were washed with tetrahydrofuran. The combined filtrates were evaporated and the residue was coevaporated several times with toluene. 3,4-Dibutyroyloxybutyl-1-phosphonic acid was obtained as an oil (190 mg, 86%) that was immediately dissolved in pyridine and used in the subsequent coupling reaction.

Step E: Preparation of 1-(3′,4′-dibutyroyloxybutylphosphonyl)-1-C-benzyloxymethyl-2,3,4,5,6-penta-O-benzyl-myo-inositol Triisopropylbenzenesulfonyl chloride (550 mg) was added to a solution of 3,4-dibutyroyloxybutyl-1-phosphonic acid (190 mg) and 1-C-benzyloxymethyl-2,3,4,5,6-penta-O-benzyl-myo-inositol (500 mg) in pyridine (15 ml) and the solution was heated for 5 hours at 60°. Water was added to the cooled solution, the solvent was evaporated and the residue was purified by column chromatography on silica gel (Merck No. 7734), eluting successively with 50:1; 25:1 and 15:1 chloroform methanol. Fractions containing the desired product were combined and evaporated to give 1-(3′,4′-dibutyroyloxybutyl-phosphonyl)-1-C-benzyloxymethyl-2,3,4,5,6-penta-O-benzyl-myo-inositol a syrup (42 mg, 6.7%). 300 MHz nmr spectrum (CD$_3$OD): δ0.88 (m, 6H, O$_2$-C—(CH$_2$)$_2$CH$_3$); 7.2–7.6 (30H, aryl).

Step F: Preparation of 1(3′,4′dibutyroyloxybutylphosphonyl)-1-C-hydroxymethyl-myo-inositol 10% Palladium-on-charcoal (50 mg) was added to a solution of 1-(3′,4′-dibutyroyloxybutylphosphonyl)-1-C-benzyloxymethyl-2,3,4,5,6-penta-O-benzyl-myo-inositol (41 mg) in glacial acetic acid (10 ml). The mixture was stirred at 25° under a stream of hydrogen for two days. The catalyst was removed by vacuum filtration and the filtrate evaporated. The residue was purified by column chromatography on silica gel (Merck No. 7734) eluting with 60:40:10 chloroform-methanol-water. Fractions containing only the desired product were combined and concentrated to give 1-(3′,4′dibutyroyloxybutylphosphonyl)-1-C-hydroxymethyl-myo-inositol as an amorphous solid (13 mg, 64%). Mass spectrum (m/e): 991 ($M^+$—$CH_3$) (per-OTMS derivative).

EXAMPLE 17

Preparation of 1-(3′,4′-dipalmitoyloxybutylphosphonyl)-1-C-hydroxymethyl-myo-inositol

Step A: Preparation of 1-(3′,4′-dipalmitoyloxybutylphosphonyl)-1-C-benzyloxymethyl-2,3,4,5,6-penta-O-benzyl-myo-inositol Triisopropylbenzenesulfonyl chloride (54 mg) was added to a solution of 3,4-dipalmitoyloxybutyl-1-phosphonic acid (270 mg) and 1-C-benzyloxymethyl-2,3,4,5,6-penta-O-benzyl-myo-inositol (500 mg) in pyridine (10 ml). The solution was heated at 60° for 48 hours and at 90° for 12 hours. Water was added to the cooled reaction and the solvent was evaporated. The residue was purified by column chromatography on silica gel (Merck No. 7734), eluting successively with 50:1, 40:1, 30:1, 20:1 and 10:1 chloroform-methanol. Fractions containing only the desired product were combined and concentrated to give a syrup: yield 290 mg (41%). 300 MHz nmr spectrum (CD$_3$OD): δ0.91 [t, 6H, —O$_2$-C—(CH$_2$)$_{14}$CH$_3$], 7.2–7.6 (30H, aryl).

Step B: Preparation of 1-(3′,4′-dipalmitoyloxybutylphosphonyl)-1-C-hydroxymethyl-myo-inositol 10% Palladium-on-charcoal (290 mg) was added to a solution of 1-(3′,4′-dipalmitoyloxy-butylphosphonyl)-1-C-benzyloxymethyl-2,3,4,5,6-penta-O-benzyl-myo-inositol (290 mg) in glacial acetic acid (25 ml). The mixture was stirred for five days at 25° under a stream of hydrogen. The reaction mixture was filtered and the catalyst washed with acetic acid followed by 60:40:10 chloroform-methanol-water. The combined filtrates were concentrated and the residue was purified by column chromatography on silica gel (Merck No. 7734) eluting successively with 40:10:1, 70:30:3 and 65:35:3.5 chloroform-methanol-water. Fractions containing only the desired product were combined and concentrated to give 1-(3',4'-dipalmitoyloxybutylphosphonyl)-1-C-hydroxymethyl-myo-inositol as an amorphous solid; yield 82 mg (54%). 300 MHz nmr Spectrum (CD$_3$OD): δ0.90 [t, 6H, —O$_2$C—(CH$_2$)$_{14}$—C$\underline{H}_3$], 1.38 (m, 48H, —O$_2$C—CH$_2$—(C$\underline{H}_2$)$_{12}$—CH$_3$).

EXAMPLE 18

5-O-(3,4-dipalmitoyloxybutylphosphonyl)-myo-inositol

Step A: Preparation of 1,2:3,4-1-, 1,2:4,5- and 1,2:5,6-dicyclohexylidene-myo-inositol A mixture of 50 g myo-inositol, 500 ml cyclohexanone, 130 ml benzene and 50 ml dimethylsulfoxide was heated to reflux and water was removed in a Dean Stark trap. 0.2 g p-Toluenesulfonic acid monohydrate was added and refluxing continued for 23 hours during which time 22 ml of water was collected. The solution was reduced in volume to a residue of 155 g by vacuum distillation and the isomers were obtained by a combination of elution chromatography on silica gel followed by recrystallization of the almost pure individual isomers to give each of the three pure isomers: 1,2:3,4-dicyclohexylidene-myo-inositol, 9.0 g, m.p. 156°–8° (lit. 158°$^{(1)}$), 9% yield; 1,2:4,5-dicyclohexylidene-myo-inositol, 9.4 g, m.p. 176°–8° (lit.$^{(1)}$ 174°), 10% yield; 1,2:5,6-dicyclohexylidene-myo-inositol, 19.1 g, m.p. 124°–6° (lit$^{(1)}$133°), 20% yield.

(1) Angyal et al., *J. Chem. Soc.*, 4116 (1961).

Step B: Preparation of 5-(and 6-)O-(3,4-dipalmitoyloxybutylphosphonyl)-1,2:3,4-dicyclohexylidene-myo-inositol A mixture of 3,4-dipalmitoyloxybutylphosphonic acid and 1,2:3,4-dicyclohexylidenemyo-inositol is treated just as in Example 1, Step C to give crude product, which is purified by preparative tlc on silica gel G to afford 5-(and 6-) O-(3,4-dipalmitoyloxybutylphosphonyl)-1,2:3,4-dicyclohexylidene-myo-inositol.

Step C: Preparation of 5-O-(3,4-dipalmitoyloxybutylphosphonyl)-myo-inositol

A sample of 5-O-(3,4-dipalmitoyloxybutylphosphonyl)-1,2:3,4-dicyclohexylidene-myo-inositol in AcOH/H$_2$O: 4/1 is heated on a steam bath and progress of the reaction is followed by tlc. When no starting material remains the solution is evaporated under reduced pressure and purified to obtain 5-O-(3,4-dipalmitoyloxybutylphosphonyl)-myo-inositol.

EXAMPLE 19

Step A: Preparation of 4-(and 3-)-O-octadecylphosphonyl-1,2:5,6-dicyclohexylideneinositol Starting with 1,2:5,6-dicyclohexylideneinositol and octadecylphosphonic acid and using the procedure described in Example 5, Step A, a mixture of 4- and 3-(octadecylphosphonyl) derivatives is obtained. The mixture is separated by thin layer chromatography on silica gel G into two discrete isomers, i.e., 4-(and 3-)-O-octadecylphosphonyl-1,2:5,6-dicyclohexylideneinositol.

Step B: Preparation of 3-O-(3,4-dipalmitoyloxybutyl phosphonyl)-4-O-octadecylphosphonyl-1,2:5,6-dicyclohexylideneinositol 4-O-Octadecylphosphonyl-1,2:5,6-dicyclohexylideneinositol obtained in Step A above is substituted for 1,2,3,4-tetra-O-benzylscylloinositol in the procedure described in Example 1, Step C, and the reaction with 3,4-dipalmitoyloxybutylphosphonic acid carried out essentially as described. The crude product is purified by preparative tlc on silica gel G plates to afford 3-O-(3,4-dipalmitoyloxybutyl phosphonyl)-4-O-octadecylphosphonyl-1,2:5,6-dicyclohexylideneinositol.

Step C: Preparation of 1-O-(3,4-dipalmitoyloxybutyl phosphonyl)-6-O-octadecylphosphonyl-myo-inositol 3-O-(3,4-dipalmitoyloxybutylphosphonyl)-4-O-octadecylphosphonyl-1,2:5,6-dicyclohexylideneinositol is heated on a steam bath in AcOH/H$_2$O:4/1 and progress of the reaction is followed by tlc. When no starting material remains the solution is evaporated under reduced pressure to obtain the desired product, 1-O-(3,4-dipalmitoyloxybutylphosphonyl)-6-O-octadecylphosphonyl-myo-inositol.

EXAMPLE 20

1,4-di-O-(dodecylphosphonyl)myo-inositol

A mixture of 1.13 g (3.33 mmole) of 1,2:4.5-dicyclohexylidene inositol, 0.84 g (3.36 mmole) of dodecanephosphonic acid, 10 ml pyridine and 2 ml trichloroacetonitrile was warmed in an oil bath. The solution was heated to reflux, cooled, reheated to reflux, cooled and kept in an oil bath at 60°–65° for 68 hours. It was cooled and evaporated under reduced pressure until pyridine began to distill. Four successive additions of hexane (10–25 ml) caused oils to precipitate and these oils were combined to give 3.25 g of crude 1,4-di-O-(dodecylphosphonyl)-1,2:4,5-dicyclohexylideneinositol.

The crude product was hydrolyzed in 48 ml glacial acetic acid and 12 ml water heated on a steam bath for 2.25 hours. On cooling overnight at 0° precipitate appeared gradually. After washing on a filter the material was dried to give 237.5 mg of 14-di-O-(dodecylphosphonyl)myo-inositol. Mass spectrum showed m/e 608 (M+ of 644-18-18) and characteristic loss of −14 increments. Mass spectrum of per-(trimethylsilyl) derivative showed m/e 1075 (hexasilyl derivative=1076) and a large peak at 1060 m/e (M+-15).

Analysis: Calcd. for C$_{30}$H$_{62}$O$_{10}$P$_2$.H$_2$O: C, 54.38; H, 9.73; P, 9.35. Found: C, 54.83; H, 10.03; P, 9.27.

EXAMPLE 21

1-O-(Octadecylphosphonyl)-myo-inositol

A mixture of 1.13 g (3.33 mmole) of 1,2:4,5-dicyclohexylidene inositol, 1.11 g (3.32 mmole) of octadecylphosphonic acid, 10 ml pyridine and 2 ml trichloroacetonitrile was heated in an oil bath. The mixture was heated to first reflux, cooled, reheated to first reflux, cooled and kept at 60°–65° for 95 hours. It was evaporated under reduced pressure at about 65° C. to remove volatiles, and a residue of 3.6 g of 3-O-(octadecylphosphonyl)-1,2:4,5-dicyclohexylideneinositol was obtained.

A sample of 3.0 g of the residue was heated for 2 hours on a steam bath in 80 ml glacial acetic acid and 20 ml water. The mixture was filtered while hot and the precipitate was washed with hot AcOH/H$_2$O:4/1. The product, 385.5 mg of 1,4-di-O-(octadecylphosphonyl)-myo-inositol was obtained.

The filtrate was cooled to 22° and more precipitation occured. This solid was filtered and dried to give 649.8 mg of crude product which was a mixture of 1- and 4-O-(octadecylphosphonyl)-myo-inositol. Mass spectrum of per (trimethylsilyl) derivative thereof showed m/e 928 and strong m/d 913 (hexa derivative M$^+$=928; m/e 913=M$^+$-15). Mass spectrum also showed strong 478 m/e (M$^+$-18=478) and 460 (M$^+$-18-18).

Analysis: Calcd. for C$_{24}$H$_{49}$O$_8$P.H$_2$O: C, 56.01; H, 9.99; P, 6.02. Found: C, 55.72; H, 10.00; P, 5.70.

EXAMPLE 22

1-O-(Octadecylphosphonyl)-6-O-p-toluene sulfonyl-myo-inositol

Step A. Preparation of 4-O-(p-toluenesulfonyl)-1,2:5,6-dicyclohexylidene-myo-inositol A solution of 339.9 mg (10 mmole) of 1,2:5,6-dicyclohexylidene-myo-inositol, 196.0 mg (1.03 mmole) of p-toluenesulfonyl chloride and 5 ml pyridine was kept at 0° for 51.5 hours. After evaporation under reduced pressure the residue was purified by chromatography on silica gel G using 10% ethyl actate in methylene chloride. Two mono-tosylates and one di-tosylate were isolated. The minor mono-tosylate, 18.9 mg, had m.p. 151°-2°, and was ascribed the 4-position for tosylation according to NMR.

Analysis: Calcd. for C$_{25}$H$_{34}$O$_8$S: C, 60.71; H, 6.93. Found: C, 60.02; H, 7.04.

Step B. Preparation of 3-O-(octadecylphosphonyl)-4-O-p-toluenesulfonyl-1,2:5,6-dicyclohexylidene-myo-inositol Starting with 4-O-(p-toluenesulfonyl)-1,2:5,6-dicyclohexyliden-myoinositol (obtained in Step A above), and octadecylphosphonic acid and using the procedure described in Example 5, Step A, there is obtained, after purification by chromatography on silica gel G, 3-O-(octadecylphosphonyl)-4-O-p-toluenesulfonyl-1,2:5,6-dicyclohexylidene-myo-inositol.

Step C. Preparation of 1-O-(octadecylphosphonyl)-6-O-p-toluenesulfonyl-myo-inositol 3-O-(octadecylphosphonyl)-4-O-p-toluenesulfonyl-1,2:5,6-dicyclohexylidene-myo-inositol is heated on a steam bath in AcOH/H$_2$O:4/1 and progress of the reaction is followed by tlc. When no starting material remains, the solution is evaporated under reduced pressure to obtain 1-O-(octadecylphosphonyl)-6-O-p-toluenesulfonyl-myo-inositol.

In the manner described in Step A of this procedure any one of the three isomeric dicyclohexylidene inositols (1,2:3,4-; 1,2:4,5-; 1,2:5,6-) may be treated with p-toluenesulfonyl chloride in pyridine and the corresponding mono-tosylates (2 from each starting material) and di-tosylates may be isolated.

For example, from 1,2:3,4-dcyclohexylidene inositol there was obtained:

A. 5-(p-toluenesulfonyl)-1,2:3,4-dicyclohexylidene inositol, m.p. 148°-50°.
Analysis: Calcd. for C$_{25}$H$_{34}$O$_8$S: C, 60.71; H, 6.93. Found: C, 60.56; H, 6.99.

B. 6-(p-toluenesulfonyl)-1,2:3,4-dicyclohexylidene inositol, m.p. 138°.
Analysis: Calcd. for C$_{25}$H$_{34}$O$_8$S: C, 60.71; H, 6.93. Found: C, 60.90; H, 7.27.

C. 5,6-di-(p-toluenesulfonyl)-1,2:3,4-dicyclohexylidene inositol, an oil.
NMR(CDCl$_3$): δ1.2–1.8 (m, C$_6$H$_{10}$ protons); 2.43 (S, CH$_3$—Ar); 2.50 (S, CH$_3$—Ar); 3.66 (d.d., C-3H); 3.98 (d.d., C-4H); 4.56–4.72 (m, C-5H and C-6H), 7.3–7.94 (d.d.d., 8 lines Ar).

Any of the obtained mono-tosylates may be substituted in Step B for 4-O-(p-toluenesulfonyl)-1,2:5,6-dicyclohexylidene-myo-inositol and treated with octadecylphosphonic acid (or another alkylphosphonic acid) and the corresponding product obtained. This product may then be treated as in Step C to hydrolyze the dicyclohexylidene protecting groups to provide the corresponding alkylphosphonyl-p-toluenesulfonyl-myo-inositol.

Furthermore, the mono- and di-tosylate derivatives may be converted to other functionalities and these derivatives may be substituted in Steps B and C to provide analogous products.

For example, 3-(p-toluenesulfonyl)-1,2:4,5-dicyclohexylidene-myo-inositol may be converted into 3-deoxy-3-azido-1,2:4,5-dicyclohexylidene-myo-inositol as shown below in Example 23.

EXAMPLE 23

3-deoxy-3-azido-1,2:4,5-dicyclohexylidene-myo-inositol

A mixture of 62.3 mg (0.126 mmole) of 3-O-(p-toluenesulfonyl)-1,2:4,5-dicyclohexylidene inositol and 80.0 mg (1.23 mmole) sodium azide in 0.4 ml dimethylformamide was heated at 140° for 3 days. The mixture was evaporated under reduced pressure to remove volatiles and the residue was extracted with methylene chloride. The extract was purified by preparative tlc on silica gel G using 10% ethyl acetate as eluant to afford 27.9 mg of 3-deoxy-3-azido-1,2:4,5-dicyclohexylidene-myo-inositol. Mass spectrum: peaks at m/e 365 (M$^+$), prominent 337 (M$^+$—N$_2$) and 322 (M$^+$—HN$_3$).

In the same manner but at reaction temperature of 120° and reaction time of 7 hours, 5-deoxy-5-azido-1,2:3,4-dicyclohexylidene-myo-inositol is obtained from 5-O-(p-toluenesulfonyl)-1,2:3,4-dicyclohexylidene-myo-inositol.

EXAMPLE 24

(1,2,3,5/4,6)-1-(3,4-dioctadecyloxylbutylphosphinyl)-methyl-2,3,4,5,6-cyclohexanepentol

Step A: Preparation of 2,3,4,5,6-penta-O-benzyl-1-C-methylene-myo-inositol n-Butyllithium (18 ml, 29 mmol; 1.6M in hexane) was added to a stirred suspension of methyltriphenylphosphonium bromide (12 g, 32 mmol) in tetrahydrofuran (80 ml) at 0°. A solution of 2,3,4,5,6-penta-O-benzyl-myo-inosose (10 g, 16 mmol) in tetrahydrofuran was added and the reaction was stirred for 18 hours. Solvent was evaporated and the residue was purified by high performance liquid chromatography (silica gel). Fractions containing 2,3,4,5,6-pento-O-benzyl-1-C-methylene-myo-inositol were combined and evaporated to afford a light yellow syrup which crystallized on standing. Trituration with light petroleum ether gave white crystals (7.2 g, 73%). Mass spectrum (m/e): 626.

Step B: Preparation of penta-O-benzyl(1,2,3,5/4,6)-1-hydroxymethyl-2,3,4,5,6-cyclohexanepentol A solution of 2,3,4,5,6-penta-O-benzyl-1-C-methylene-myo-inositol (7.2 g, 11.5 mmol) in tetrahydrofuran (72 ml) was added to a solution of 0.50M 9-borabicyclo [3.3.1] nonane (144 ml, 72 mmol) in hexane. The resulting solution was heated at reflux temperature for 18 hours. After cooling to room temperature, ethanol (48 ml) was added dropwise followed by 2.5N sodium hydroxide (35 ml) and 30% hydrogen peroxide (29 ml). The reaction mixture was heated for 1 hour at 50°. After cooling to room temperature, the aqueous phase was saturated with potassium carbonate. The layers were separated and the organic phase was evaporated. The epimeric mixture of alcohols was separated from by-products by high performance liquid chromatography (silica gel) eluting with 1:1 diethyl ether-hexane.

The mixture of alcohols (7.2 g) was dissolved in pyridine (240 ml) and the solution was cooled to 0°. Acetic anhydride (48 ml) was added and the reaction mixture was allowed to stand at room temperature for 18 hours before being poured into ice-water. The aqueous mixture was extracted with three portions of ether and the combined ethereal extracts were washed with 1N hydrochloric acid, saturated aqueous sodium hydrogen carbonate and saturated aqueous sodium chloride. The solvent was removed by evaporation and penta-O-benzyl(1,2,3,5/4,6)-1-acetoxymethyl-2,3,4,5,6-cyclohexanepentol was obtained by high performance liquid chromatography (silica gel) eluting with 7.5:1 hexane-ethyl acetate.

A catalytic amount of sodium methoxide was added to a solution of penta-O-benzyl(1,2,3,5/4,6)-1-acetoxymethyl-2,3,4,5,6-cyclohexanepentol (2.6 g) in methanol (48 ml) and dichloromethane (14 ml) and the reaction mixture was allowed to stand at room temperature for 18 hours. The solvent was evaporated and the residue was partitioned between diethyl ether and water. The layers were separated and the organic layer was washed with water and saturated aqueous sodium chloride, dried (sodium sulfate) and evaporated to give penta-O-benzyl-(1,2,3,5/4,6)-1-hydroxymethyl-2,3,4,5,6-cyclohexanepentol (2.3 g, 31%) as a colorless syrup. Mass spectrum: 553 m/e (CH$_2\phi$).

Step C: Preparation of penta-O-benzyl 1,2,3,5/4,6-1-chloromethyl-2,3,4,5,6-cyclohexanepentol Thionyl chloride (0.30 ml, 0.48 g, 4.0 mmol) is added dropwise to a solution of penta-O-benzyl (1,2,3,5/4,6)-1-hydroxymethyl 2,3,4,5,6-cyclohexanepentol (2.3 g, 3.6 mmol) in diethyl ether (50 ml) containing pyridine (0.35 ml, 0.34 g, 4.3 mmol) at 0°. When addition is complete, the mixture is stirred at ambient temperature for 3–4 hours. The reaction mixture is poured slowly into saturated aqueous sodium hydrogen carbonate and the resulting mixture is extracted with three portions of ether. The combined ethereal extracts are washed with water and saturated sodium chloride, dried (sodium sulfate) and evaporated. The residue is purified by column chromatography on silica gel (E-Merck, No. 7734) eluting successively with 15:1 and 5:1 hexane-ethyl acetate affording penta-O-benzyl (1,2,3,5/4,6)-1-chloromethyl-2,3,4,5,6-cyclohexanepentol (1.6 g, 70%).

Step D: Preparation of penta-O-benzyl (1,2,3,5/4,6)-1-(dichlorophosphinyl)methyl-2,3,4,5,6-cyclohexanepentol Penta-O-benzyl(1,2,3,5/4,6)-1-chloromethyl-2,3,4,5,6-cyclohexanepentol (1.6 g, 2.4 mmol) is added to a vigorously stirred suspension of aluminum chloride (0.64 g, 4.8 mmol) and phosphorus trichloride (1.3 g, 2.0 mmol) at 45° and heating is continued until all the aluminum chloride is dissolved. The complex is cooled, dissolved in dichloromethane (50 ml), and dibutyl phthalate (2.4 g, 8.7 mmol) and finely divided antimony (0.29 g, 2.3 mmol) are added. The mixture is then heated for 4 hours at 85°. The reaction is cooled and the dichloromethane is evaporated. The residue is purified by vacuum distillation affording penta-O-benzyl(1,2,3,5/4,6)-1-(dichlorophosphinyl)-methyl-2,3,4,5,6 cyclohexanepentol (0.52 g, 30%).

Step E: Preparation of penta-O-benzyl(1,2,3,5/4,6)-1-(dibenzyloxyphosphinyl)methyl-2,3,4,5,6-cyclohexanepentol To a solution of benzyl alcohol (0.15 g, 1.4 mmol) and triethylamine (0.14 g 1.4 mmol) in ether (15 ml) at −10° is added a solution of penta-O-benzyl (1,2,3,5/4,6)-1-(dichlorophosphinyl)methyl-2,3,4,5,6-cyclohexanepentol (0.52 g, 0.71 mmol) in ether (5 ml). The mixture is heated at reflux temperature for 2.5 hours. The reaction is cooled to room temperature and the precipitate is removed by vacuum filtration and washed with ether. The combined filtrates are concentrated and the product is purified by column chromatography on silica gel (E. Merck, No. 7734) eluting successively with 15:1, 10:1, 5:1 and 1:1 hexane-diethyl ether, yielding penta-O-benzyl-(1,2,3,5/4,6)-1-(dibenzyloxyphosphinyl)methyl-2,3,4,5,6-cyclohexanepentol (0.31 g, 50%).

Step F: Preparation of penta-O-benzyl(1,2,3,5/4,6)-1-[benzyl(3,4-dioctadecyloxybutyl)phosphinyl]methyl-2,3,4,5,6-cyclohexanepentol A solution of 3,4-dioctadecyloxybutyl-1-bromide (0.24 g, 0.36 mmol; prepared by the procedure set forth in A. F. Rosenthal et al., *J. Chem. Soc.* (1965) 345) and penta-O-benzyl (1,2,3,5/4,6)-1-(dibenzyloxyphosphinyl)methyl-2,3,4,5,6-cyclohexanepentol (0.31 g, 0.36 mmol) in 2-methoxyethyl ether (5 ml) is heated at 120° for 40 hours under a nitrogen atmosphere. The 2-methoxyethyl ether is removed by evaporation under reduced pressure and the residue is purified by column chromatography on silica gel (E. Merck, #7734) eluting successively with 100:1, 50:1, 25:1, 5:1 and 1:1 hexane-ethyl acetate affording penta-O-benzyl-(1,2,3,5/4,6)-1-[benzyl-(3,4-dioctadecyloxybutyl)-phosphinyl]methyl-2,3,4,5,6 cyclohexanepentol (0.20 g, 40%).

Step G: Preparation of (1,2,3,5/4,6-1)-(3,4-dioctadecyloxybutylphosphinyl)-methyl-2,3,4,5,6-cyclohexanepentol 10% Palladium on carbon (0.20 g) is added to a solution of penta-O-benzyl-(1,2,3,5/4,6)-1-[benzyl-(3,4-dioctadecyloxybutyl)-phosphinyl]methyl-2,3,4,5,6-cyclohexanepentol (0.20 g, 0.14 mmol) in glacial acetic acid (5 ml) and the mixture is stirred for 18 hours at ambient temperature under a stream of hydrogen. The reaction mixture is filtered and the catalyst is washed with acetic acid followed by 6:4:1 chloroform/methanol/water. The combined filtrates are evaporated and the residue is purified by column chromatography on silica gel (E. Merck #7734) eluting successively with chloroform, 9:1 chloroform/methanol, 90:10:1, 40:10:1, 70:30:3 and 6:4:1 chloroform/methanol/water. Evaporation of the appropriate fractions affords (1,2,3,5/4,6)-1-(3,4-dioctadecyloxybutylphosphinyl)-methyl-2,3,4,5,6-cyclohexanepentol (0.10 g, 80%).

What is claimed is:

1. A compound of formula:

$$L-\overset{O}{\underset{OR}{\overset{\|}{P}}}-Y-A \quad (I)$$

or a pharmaceutically acceptable acid, ester, ether or carbonate thereof, wherein:

L is
 (a) hydrogen;
 (b) $R^1$; where $R^1$ is
  (1) straight or branched-chain alkyl having from 1 to 20 carbon atoms especially $C_{1-6}$ alkyl;
  (2) aryl having from 6 to 10 carbon atoms;
  (3) cycloalkyl having from 3 to 8 carbon atoms;
  (4) alkenyl having from 2 to 20 carbon atoms especially $C_{8-20}$ alkenyl;
  (5) cycloalkenyl having from 5 to 8 carbon atoms;
  (6) aralkyl, alkaryl, aralkenyl, alkenylaryl wherein alkyl, aryl, and alkenyl are as previously defined;
  The above groups (1) to (6) are unsubstituted or substituted by hydroxy; alkoxy; halo; cyano; carboxy; amino; substituted amino; carbamoyl; sulfonyl; sulfinyl; thio; alkylthio; or nitro;
 (c)

$$\underset{CH_2-CH_2-(CH_2)_n-}{\overset{OR^2 \quad OR^3}{| \quad \quad |}}$$

where $R^2$ and $R^3$ independently are:

(1) $R^1$;
 (2) $-\overset{O}{\overset{\|}{C}}-R^1$;
 (3) $-\overset{O}{\overset{\|}{C}}-O-R^1$;
 (4) $-\overset{O}{\overset{\|}{C}}-NHR^1$;
 (5) $-\overset{O}{\overset{\|}{C}}-SR^1$;
 (6) $-\overset{O}{\underset{O}{\overset{\|}{\underset{\|}{P}}}}-O-R^1$;

n is an integer from 1 to 4; or
 (d)

$$\underset{CH_2-CH-(CH_2)_n-}{\overset{R^2NH \quad NHR^3}{| \quad \quad |}}$$

wherein $R^2$, $R^3$, and n are as defined previously;

R is
 (a) hydrogen;
 (b) loweralkyl;
 (c) cycloalkyl having from 3 to 8 carbon atoms; or
 (d) aralkyl; Y is oxygen or methylene; and A is a radical of
  (a) myo-inositol or a configuration isomer thereof;
  (b) branched chain myo-inositol;
  (c) 2-,4 or 5-positional isomer of myo-inositol;
  (d) inositol substituted with amino; azido; deoxy; halo; or
  (e) branched-chain inositol of the structural formula (e);

[structure (e): cyclohexane ring with OH, OH, OH, OH, OH substituents and $R^4$]

where $R^4$ is $C_{1-6}$ alkyl or substituted $C_{1-6}$ alkyl;
 (f) phosphoryl inositols having one or more of its hydroxy groups coupled with another $$-\overset{O}{\underset{OR}{\overset{\|}{P}}}-L$$

group; or
 (g) epimeric myo-inositol.

2. The compound of claim 1 wherein:

L is
 (a) $R^1$; or
 (b)

$$\underset{CH_2-CH_2-(CH_2)_n}{\overset{OR^2 \quad OR^3}{| \quad \quad |}}$$

where $R^2$ and $R^3$ are as previously defined;

R is
 (a) hydrogen;
 (b) $C_{1-6}$alkyl; or
 (c) benzyl;

Y is oxygen or methylene; and
A is a radical of
 (a) myo-inositol;
 (b) branched-chain myo-inositol;
 (c) branced-chain inositol of formula (e);
 (d) epimeric myo-inositol;
 (e) phosphoryl inositol having one or more of its hydroxy groups coupled with another $$-\overset{O}{\underset{OR}{\overset{\|}{P}}}-L$$

group.

3. The compound of claim 1 wherein:
L is
 (a)

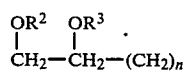
where $R^2$ and $R^3$ independently are
(1) $R^1$ where $R^1$ is $C_{7-20}$ alkyl;
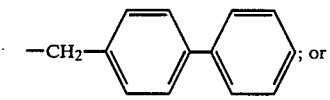
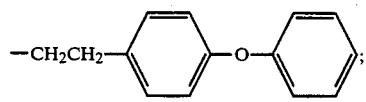
(2)
where $R^1$ is $C_{7-20}$ alkyl,
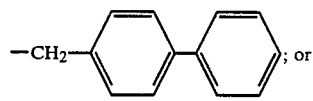
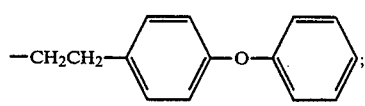
(3)
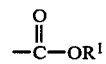
where $R^1$ is $C_{7-20}$ alkyl; or
(b) straight or branched $C_{7-20}$ alkyl;
n is 1–2;
R is hydrogen or $C_{1-6}$ alkyl;
Y is oxygen; and
A is a radical of myo-inositol.
* * * * *